United States Patent [19]

Evans

[11] Patent Number: 5,122,133
[45] Date of Patent: Jun. 16, 1992

[54] COMPRESSION SCREW FOR A JOINT ENDOPROSTHESIS

[75] Inventor: David L. Evans, Bartlett, Tenn.
[73] Assignee: Smith & Nephew Richards Inc., Memphis, Tenn.
[21] Appl. No.: 603,799
[22] Filed: Oct. 26, 1990
[51] Int. Cl.⁵ .................................................. A61F 2/02
[52] U.S. Cl. ........................................ 606/73; 606/72; 606/60
[58] Field of Search .............. 606/53, 60, 62, 63, 606/66, 72, 73, 74

[56] References Cited

U.S. PATENT DOCUMENTS

| | | | |
|---|---|---|---|
| 4,095,591 | 6/1978 | Graham, Jr. et al. | 128/92 BB |
| 4,383,527 | 5/1983 | Asnis et al. | 128/92 EB |
| 4,432,358 | 2/1984 | Fixel | 128/92 BB |
| 4,438,762 | 3/1984 | Kyle | 606/65 |
| 4,450,835 | 5/1984 | Asnis et al. | 128/92 EB |
| 4,530,355 | 7/1985 | Griggs | 128/92 BB |
| 4,612,920 | 9/1986 | Lower | 128/92 BA |
| 4,621,629 | 11/1986 | Koeneman | 128/92 YS |
| 4,628,923 | 12/1986 | Medoff | 128/92 YV |
| 4,640,271 | 2/1987 | Lower | 606/65 |
| 4,653,489 | 3/1987 | Tronzo | 128/92 YV |
| 4,657,001 | 4/1987 | Fixel | 128/92 YS |
| 4,776,329 | 10/1988 | Treharne | 128/92 YR |
| 4,791,918 | 12/1988 | Von Hasselback | 128/924 K |
| 4,794,919 | 1/1989 | Nilsson | 128/92 YK |
| 4,858,601 | 8/1989 | Glisson | 128/92 R |
| 4,940,467 | 7/1990 | Tronzo | 606/66 |

FOREIGN PATENT DOCUMENTS 551875  10/1956  Belgium .............................. 606/66

OTHER PUBLICATIONS

"Hip Nails For All Occasions", By Raymond G. Tronzo, M.D., *Orthopedic Clinics of North America*, vol. 5, No. 3, Jul. 1974.

*Primary Examiner*—Robert A. Hafer
*Assistant Examiner*—Sam Rimell
*Attorney, Agent, or Firm*—Pravel, Gambrell, Hewitt, Kimball & Krieger

[57] ABSTRACT

A compression bone screw apparatus includes an elongated cylindrical shaft member with a first smaller diameter portion that is of generally uniform cylindrical configuration, and a second enlarged diameter annular proximate end portion. An internal bore extends longitudinally along the length of the shaft member, being open ended so that a driver tool can extend through the elongated cylindrical shaft member during installation of the compression bone screw apparatus. A generally cylindrical lag screw member is slidably mounted in telescoping fashion upon the shaft member and at a position spaced from the annular proximate end portion thereof. Splines prevent rotation of the shaft with respect to the lag as the lag slides upon the shaft to increase the overall combined length of the assembled shaft and lag screw. Stops, preferably in the form of abutting shoulders of the respective shaft and lag screw members abut when the apparatus is fully extended so that continued threading of the lag into a surgical opening in bone causes a compression load across a fracture. The small compression load discourages disassembly of the apparatus when subsidence occurs.

8 Claims, 7 Drawing Sheets

COMPRESSION SCREW FOR A JOINT ENDOPROSTHESIS

BACKGROUND OF THE INVENTION

1. Field of the Invention

The present invention relates to orthopedic fixation devices for use with modular joint implants and more particularly relates to an improved compression screw apparatus for retaining a joint endoprosthesis in a bone wherein the screw is held in position by a small compressing load, and applied by a part of the implant assembly. The compression load prevents a screw backing out as the prosthesis sinks into the bone (subsides). The screw is particularly suitable for use with tibial prostheses.

2. General Background

Fixation screws and nails used in modular joint replacement can sometimes "back out" of proper operative position if the implant subsides. Revision surgery can be required to reassemble and/or replace all or part of the implant device. Several prior art devices used to treat fractures of the hip are discussed and illustrated in an article entitled "Hip Nails For All Occasions" by Raymond G. Tronzo, in the *Orthopedic Clinics of North America* (Vol. 5, No. 3, July 1974).

A number of bone screws are commercially available or the subject of publications which are retained in position by means of nuts, threads, pins, retaining rings, welds or lock washers. These retainers physically secure the screw in position. Certain disadvantages are present in known mechanical screw retainers if used for fixation of a modular joint replacement. Such mechanical retainers would be subject to fatigue loads, which have a high likelihood of causing failure of the mechanical retention used, resulting in a disassembly of the implant device.

Another disadvantage of prior fixation systems is that in most cases they require additional surgical time for use and are subject to error. The potential negative effects of prolonged surgery include numerous complications, and errors that may lead to failure which injures the patient, requiring additional surgery.

Several orthopedic fixation devices have been patented. The Asnis system shown in U.S. Pat. Nos. 4,383,527 and 4,450,835 uses one or more rigid lag screws which are installed across a fracture site over guide pins to rigidly secure the bone fragments in close proximity to one another.

Other devices for the fixation of fractures have been patented. A variable length fixation device for insertion into a hole formed in two or more bone fragments includes a barrel portion and a fastener element. The barrel portion is secured to an inside surface of the hole in a proximal one of the bone fragments. The fastener element is telescopically mounted to the barrel portion and is extendable into the distal of one of the bone fragments. The assembly prevents lateral movements of the distal fragments, relative to the proximate fragment, while allowing axial relative movements (i.e., linear movements along the longitudinal axis of the fastener element) to occur. In one embodiment, the fastener element is a cannulated bone screw having a hexagonal shaped cross section on one end which is telescopically received into a hex shape interior of the hollow barrel portion. Two components are preferably permanently joined to form a one-piece assembly having a variable overall length. The fixation device is substantially insertable in its entirety into a hole which extends across the fracture site.

Other patents that relate generally to compression screws include U.S. Pat. No. 4,776,329, entitled "Resorbable Compression Screw And Method", wherein a method for repairing a bone fracture with a compression screw assembly is provided. First and second non-resorbable compression members are positioned so that the head portion of the compression screw can protrude from the surface of the second non-resorbable compression member after further compression is effected by the normal healing process. At least the head portion of the screw is formed of a material that resorbs upon contact with body fluids.

In U.S. Pat. No. 4,530,355, there is provided a compression screw assembly for applying compression to a fracture bone. The apparatus includes a lag screw, a compression plate including a hollow barrel member adapted to receive the lag screw in at least one fixed orientation, a wrench assembly adapted to releasably engage the lag screw in axial alignment therewith, and apparatus having surface contours complimentary with the outer surface of the lag screw and inner surface of the barrel member for being optionally insertable into the barrel member to prevent axial rotation of the lag screw with respect to the barrel member.

Another compression screw system is the subject of U.S. Pat. No. 4,095,591, wherein an extension is provided for being non-rotatably fixed to a lag screw that is to be anchored to the head of a femur or other bone in a manner so as to allow compression to be applied to the fracture. The extension extends outward of the bone when attached to the lag screw and when the lag screw is anchored to the bone to allow a compression plate to be easily positioned thereon, the cross section of the extension is substantially the same as the cross section of the lag screw to allow the compression plate to be easily and quickly passed onto the lag screw from the extension once the compression plate has been positioned on the extension.

Other fixating devices which uses bone screws include U.S. Pat. No. 4,432,358, entitled "Compression Hip Screw Apparatus"; U.S. Pat. No. 4,530,355, entitled "Compression Screw Assembly"; U.S. Pat. No. 4,612,920, entitled "Compression Hip Screw"; U.S. Pat. No. 4,621,629, entitled "Compression Hip Screw"; U.S. Pat. No. 4,628,923, entitled "Axial Compression Device"; U.S. Pat. No. 4,653,489, entitled "Fenestrated Hip Screw And Method Of Augmented Fixation"; U.S. Pat. No. 4,657,001, entitled "Antirotational Hip Screw"; U.S. Pat. No. 4,791,918, entitled "Femoral-Neck Implant"; U.S. Pat. No. 4,794,919, "Fixating Device"; and U.S Pat. No. 4,858,601, entitled "Adjustable Compression Bone Screw".

SUMMARY OF THE INVENTION

The present invention provides an improved compression bone screw apparatus, having particular utility as a compression screw for a joint endoprothesis. The apparatus is designed to solve the problem of preventing fixation screws from backing out when a modular joint replacement implant subsides. If the fixation screws back out, disassembly of the implant may result. Revision surgery will then be required to reassemble/replace all or a portion of the device.

The present invention avoids screw back out by compressing when the modular joint implants subsides. This is accomplished by a two-piece design of the screw apparatus which allows compression from the fully extended position when a small compressing load is applied to the screw.

The screw apparatus of the present invention also features an angled or dished, generally convex top surface of the head portion which allows the plate into which the screw is fixed to tilt about the spherical radius center of the head without the screw protruding above the plate. This reduce the chance that tilting subsidence will lead to screw back out and disassembly of the device.

The above discussed several prior art devices include screws which are retained in position by means of nuts, threads, pins, retaining rings, welds, lock washers, metal deformation (peening, for example). All of these securing means physically secure the screw in position. With the present invention, the screw is not held in position except by means of a small compression load, applied by a portion of the joint implant assembly. With the present invention, the problem of fatigue loads which are associated with the above-discussed prior art designs, is eliminated. Fatigue loads have a high likelihood of causing failure of the retention means of any system, which may lead to a disassembly of the entire device and mechanical failure. The present invention will allow relief of fatigue loads which may occur in subsidence, thus avoiding disassembly and mechanical failure of the device.

Other disadvantages of similar devices is that in most instances they require additional surgical time for use and are subject to error. This introduces the potential negative effects of prolonged surgery and include increased incidence of commercial complications. Surgical errors may also lead to failures which injure the patient and may require additional surgery.

The present invention thus provides an improved compression screw bone apparatus having particular utility in use with a joint endoprothesis. The apparatus includes an elongated cylindrical shaft member that has a first small diameter portion and an enlarged diameter annular proximate end or head portion. An internal bore extends longitudinally along the length of the shaft member, and a generally cylindrical lag screw with an internal lag bore is slidably mounted in telescoping fashion upon the shaft member and at a position spaced from the annular proximate end portion thereof. External threads are provided on the lag screw for engaging a surgically formed opening in bone tissue.

The lag screw bore is elongated so that the shaft can extend into the lag screw socket, along substantially the entire length of the lag screw if necessary. The lag slides to a fully extended position upon the shaft which increases the overall combined length of the assembled shaft and lag screw member to maximum diameter. The lag then bottoms out and can extend no further, and compression loading is then provided. Thus when the assembly is fully extended into a surgical opening a compression load is placed across the fracture.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENTS

Figure 1:
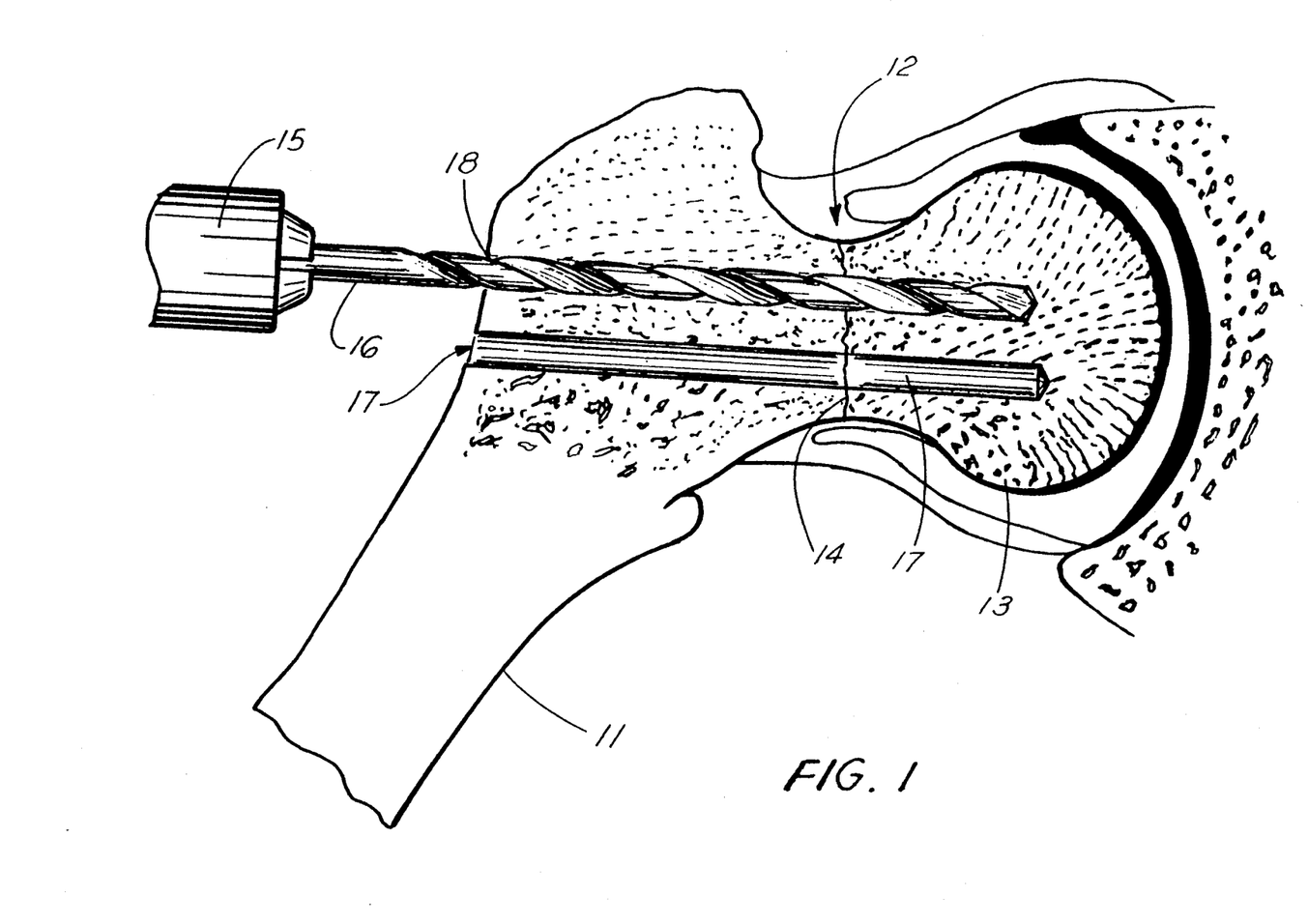
FIG. 1 is a schematic side sectional view illustrating the drilling of a opening in bone tissue prior to insertion of the compression screw apparatus of the present invention.
Figure 2:
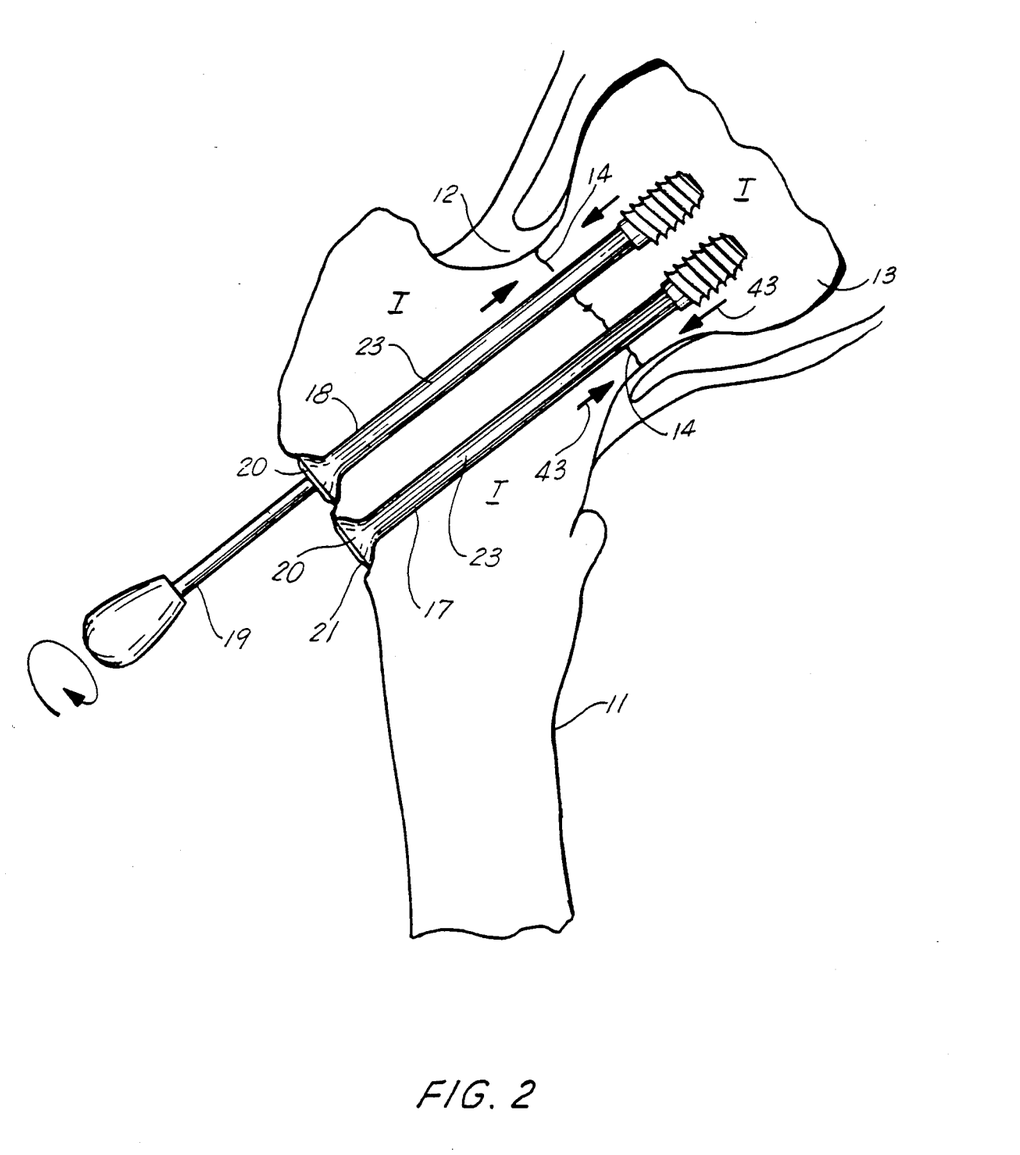
FIG. 2 is a sectional elevational view of the preferred embodiment of the apparatus of the present invention illustrating placement.

FIGS. 1-10 illustrate generally the preferred embodiment of the apparatus of the present invention designated generally by the numeral 10. In FIG. 1, there can be seen a patient's femur 11 and illustrating schematically the neck 12, ball 13, and a fracture site 14. A drill 15 is shown in fragmentary view as supporting an elongated drill bit 16 which is forming a pair of spaced apart openings 17, 18. In FIG. 2, a driver tool 19 (see FIG. 6) is used by the surgeon to thread the apparatus 10 into operating position within one of the surgically formed openings 17, 18.

Figure 6:
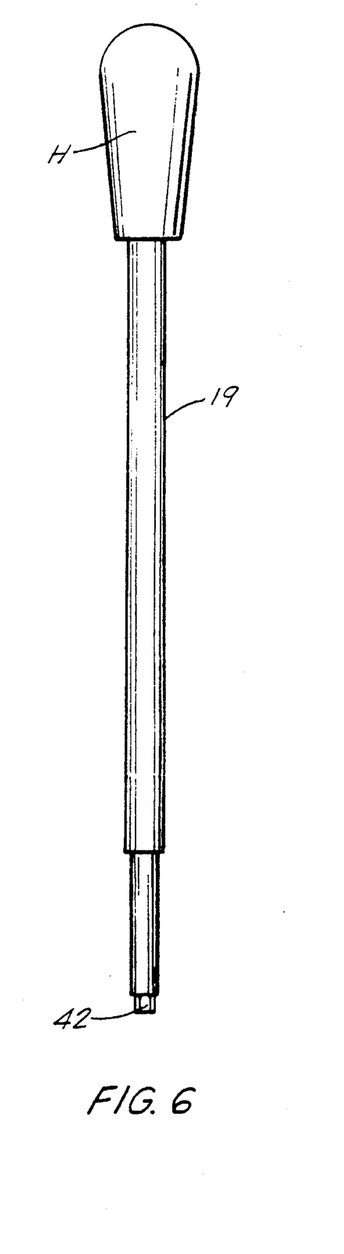
FIG. 6 is a side view of a driver tool used to install the compression screw apparatus of FIGS. 2-5.

The driver tool extends into an open ended bore 28 that extends longitudinally along the central axial portion of shaft 23 which has a proximate end 20 portion with an angled or convex top 21. The shaft 23 as aforementioned is hollowed, providing a central, longitudinally extending cylindrical bore 28 that can accommodate driver tool 19.

A curved transition section forms an interface between the enlarged head 20 and shaft 23. The shaft 23 is generally cylindrical, providing a cylindrical outer surface that extends between the transition section 24 and shoulder 26 which is an annular shoulder defining a change in diameter of the shaft 23 and communicating with an enlarged diameter annular end portion 27.

Figure 3:
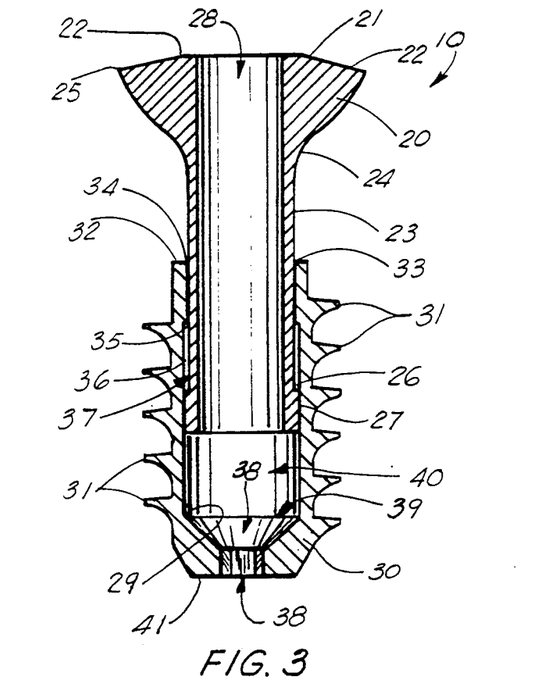
FIG. 3 is a sectional view of the preferred embodiment of the apparatus of the present invention.
Figure 4:
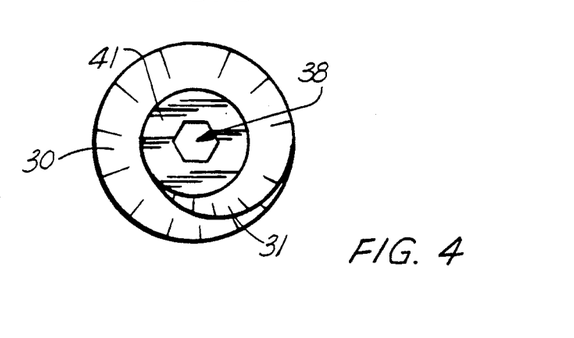
FIG. 4 is a bottom or distal end view of the preferred embodiment of the apparatus of the present invention.
Figure 5:
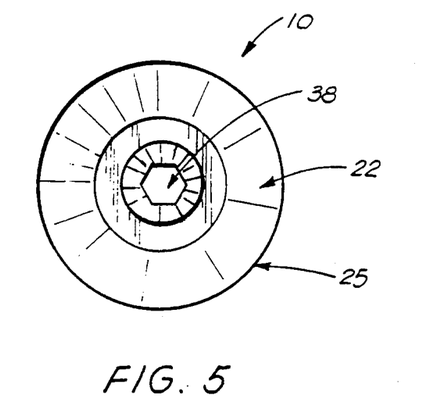
FIG. 5 is a top or proximate end view of the preferred embodiment of the apparatus of the present invention.
Figure 7A:
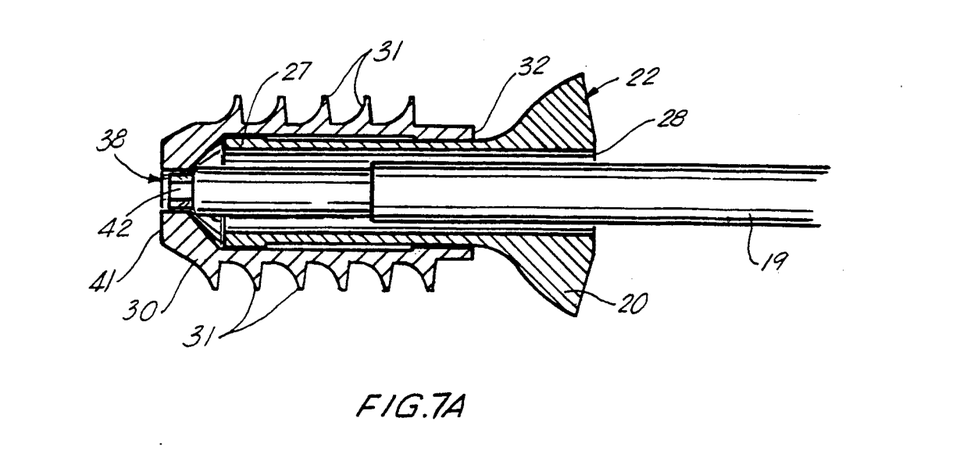
FIGS. 7A-7C are sequential sectional side views illustrating installation of the preferred embodiment of the apparatus of the present invention using a driver tool.
Figure 7B:
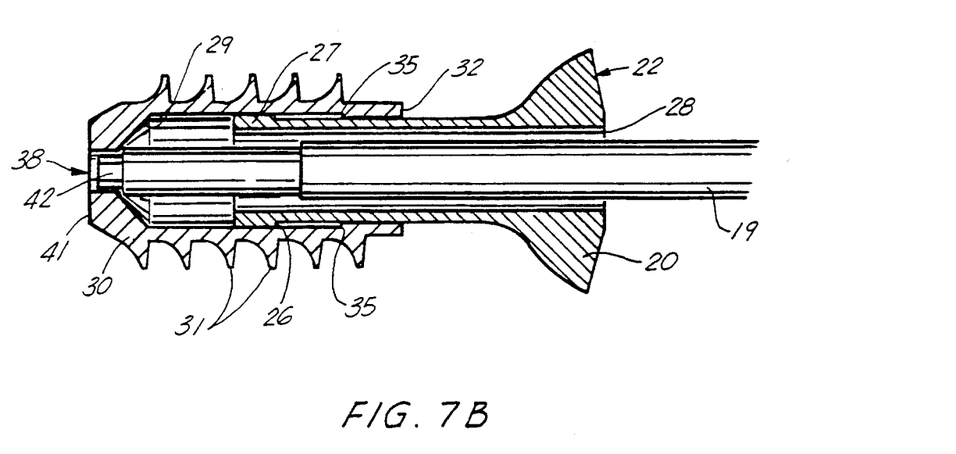

A lag sleeve 30 is slidably and telescopically mounted upon shaft 23. Lag sleeve 30 provides at least one external thread 31. The proximate end or upper end 32 of lag 30 defines an opening 34 having an internal diameter that is substantially equal to the external diameter of shaft 23 above enlarged diameter portion 27, as shown in FIG. 3. The upper end 32 of lag 30 defines thus a cylindrical sleeve 33 that closely fits and slides upon the shaft 23 above portion 27. An internal annular shoulder 35 defines a change in diameter of the internal bore 40 of lag 30. Shoulder 35 communicates with the inside surface of sleeve 33 and also with an enlarged diameter bore section 36 of bore 40. The lag sleeve can be heated, e.g., to install shaft 23 therein. Thus, upon assembly, there is a space 37 between the inner cylindrical wall 36 of lag 30 and the outer surface of shaft 23 when the shoulder 26 of shaft 23 and the shoulder 35 of lag 30 are spaced apart, as shown in FIGS. 3 and 7A-7B. The lower end portion 41 of lag 30 provides a hexagonal socket 38 that communicates with bore 40, as shown in FIG. 3.

Figure 7C:
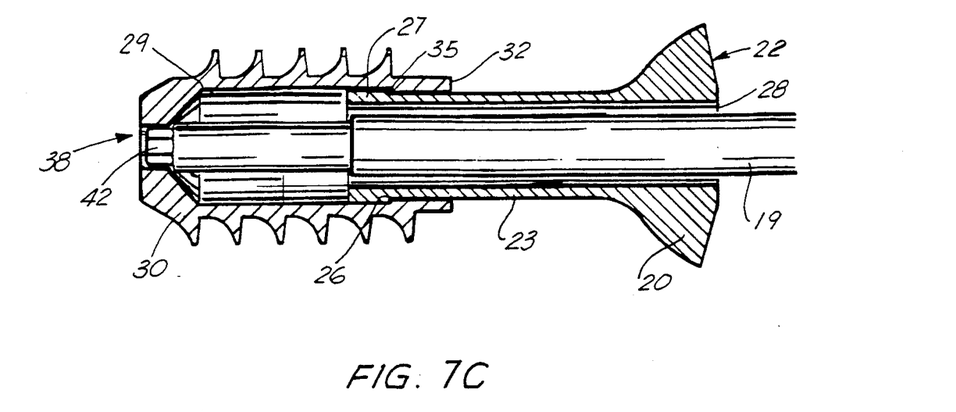
Figure 8:
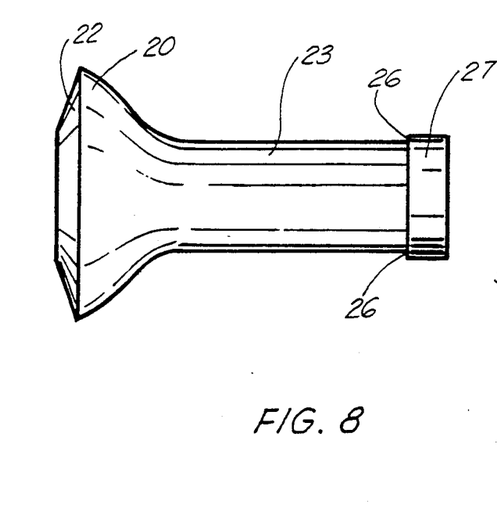
FIG. 8 is a partial view of the preferred embodiment of the apparatus of the present invention illustrating the proximate head portion thereof.
Figure 9:
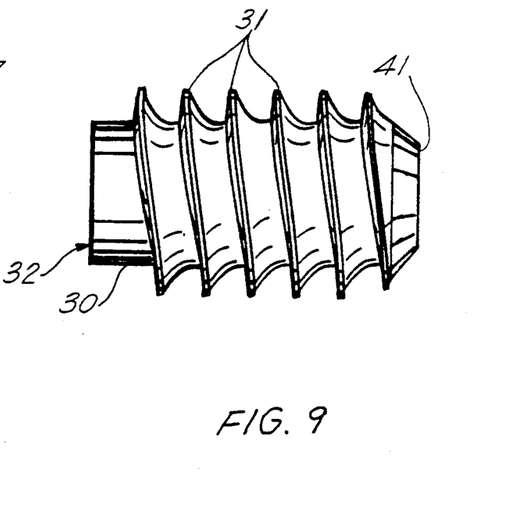
FIG. 9 is a fragmentary view of the preferred embodiment of the apparatus of the present invention illustrating the sliding lag sleeve portion thereof.

Cylindrical bore 28 is sized to accommodate driver 19 and the driver 19 provides a hexagonal drive tip 42 that is sized to register in and fit a tooled hexagonal socket 38 (see FIGS. 7A-7C). In this manner, the surgeon uses the driver 19 to rotate the lag screw 30 portion of the apparatus 10. During use, the surgeon inserts the distal end 41 of lag screw 30 into one of the openings 17, 18 formed in the bone tissue T, as shown in FIG. 2. The surgeon then threads the lag 30 into the bone tissue at one of the openings 17 and 18. The lag 30 portion rotates with the driver and separately with respect to the shaft 23. This allows the lag 30 to continue to rotate after the head 20 portion abuts and registers against a bone plate, prosthesis, or simply at the outer surface of the patient's femur 11 as shown in FIG. 2. By continuing to rotate the driver 19 and applying torque at the handle H, the surgeon continues to rotate the lag 30. However, frictional resistance between the bone tissue and the head 20 causes the head and shaft 23 to cease rotation and further advancement while the lag 30 continues to advance. This causes a resistance in torque to dramatically increase so that a compression load is placed in the tissue T, as shown by the arrows 43 in FIG. 2.

The two-part apparatus 10 allows compression from the fully extended position (FIGS. 2 and 7C) when a small compressing load is applied to the screw. The apparatus 10 will allow relief of fatigue loads which may occur in subsidence, thus avoiding disassembly and mechanical failure of the device in a relevant range of subsidence (relevant range is defined as an insufficient amount of subsidence to require surgical replacement of a modular implant for reasons other than mechanical failure of the implant).

FIGS. 7A-7C illustrate sequentially, the installation of the apparatus 10 of the present invention. The screw 10 is inserted into the surgical hole or opening. Initially, the enlarged end 27 registers with the stop 29 portion of the lag 30 (FIG. 7A). The surgeon then rotates the handle H of the driver 19 rotating the threads 31 of the lag 30 into the opening and continuing. As the screw head 20 begins to engage an endoprothesis, or bone tissue, resistance causes the lag 30 to slide along the shaft 23, and intermediate sliding position being illustrated in FIG. 7B.

Continued in advancement of the lag 30 into the surgical opening 17 or 18 causes the lag 30 to become fully extended so that the shoulder 26 of the shaft 23 engages the shoulder 35 of the lag 30, as shown in FIG. 7C. At this point, the lag can slide no further with respect to the shaft 23, and the torque resistance dramatically increases. The shoulders 26 and 35 abut upon full extension (FIG. 7C) to prevent further advancement, and the screw 10 will then "lag" (apply compression to the implant bone assembly).

Figure 10:
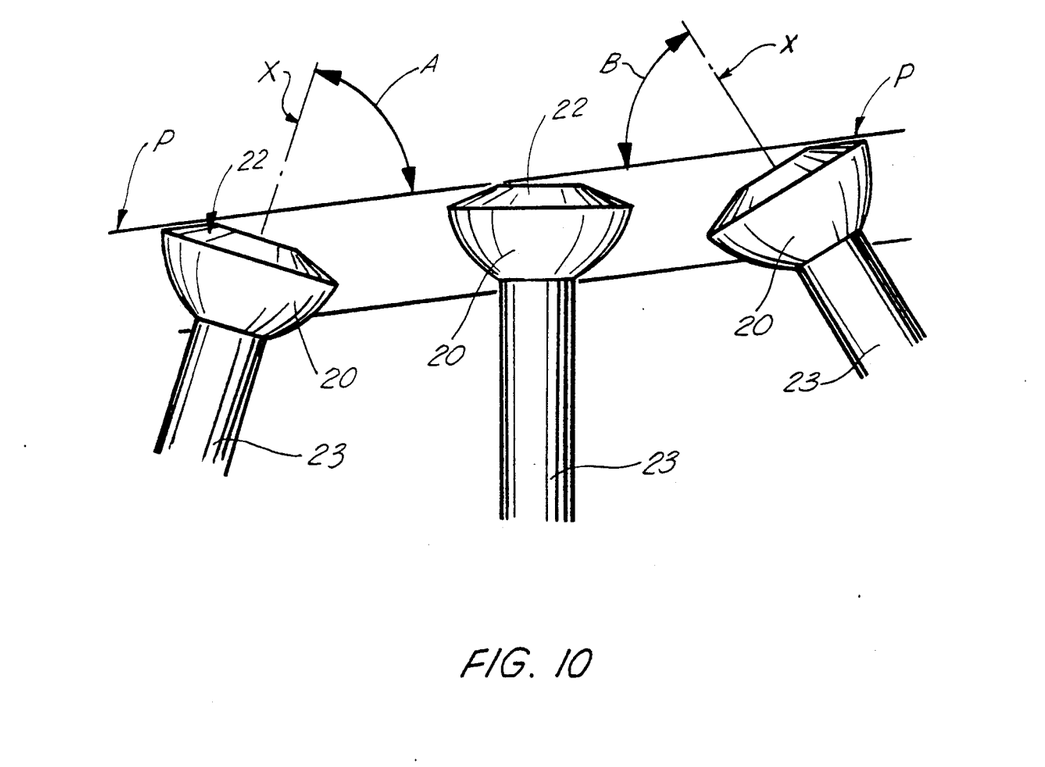
FIG. 10 is a schematic side fragmentary view of the preferred embodiment of the apparatus of the present invention illustrating plate portion and screw portions geometry when the screw tilts with respect to the plate portion.

In FIG. 10, an endoprosthesis plate P is illustrated schematically in a side view with the head 20 portion of the apparatus 10 being shown in various positions. The central longitudinal axis of the shaft 23 indicated by the letter "X" is illustrated in different angular positions with respect to the outer surface of the plate P as shown by the angles A and B in FIG. 10. The use of an angled top 21 having the annular beveled surface 22 allows the plate P into which the screw 10 is fixed to tilt about the spherical radius center of the head 20 without the screw 10 protruding above the plate P. This reduces the chance that tilting subsidence will lead to screw back out and disassembly of the device.

Figures 11, 12, 13:
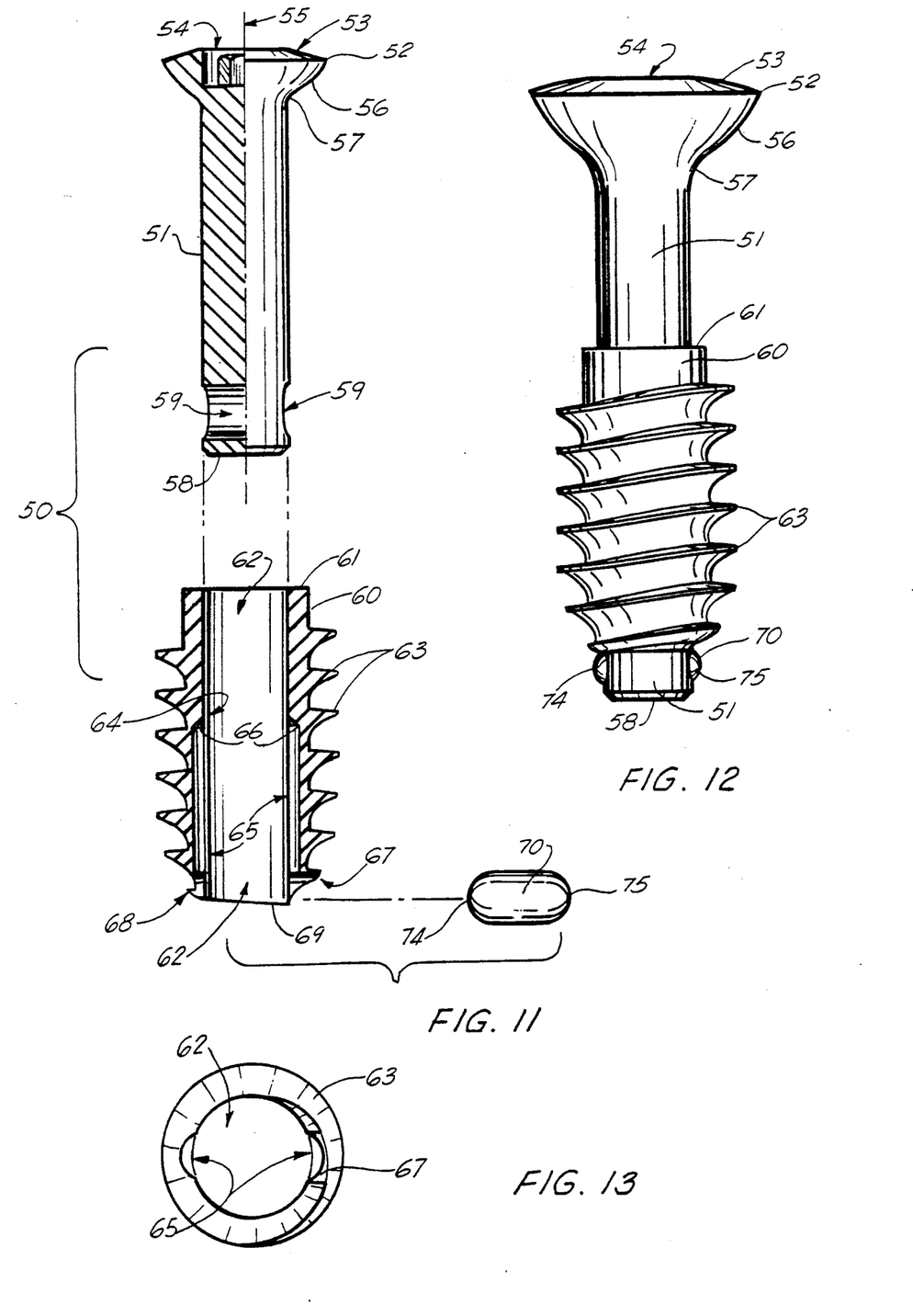
FIG. 11 is an exploded view of a second embodiment of the apparatus of the present invention.
FIG. 12 is a side view of a second embodiment of the apparatus of the present invention.
FIG. 13 is a distal or bottom end view of a second embodiment of the apparatus of the present invention.
Figure 14A:
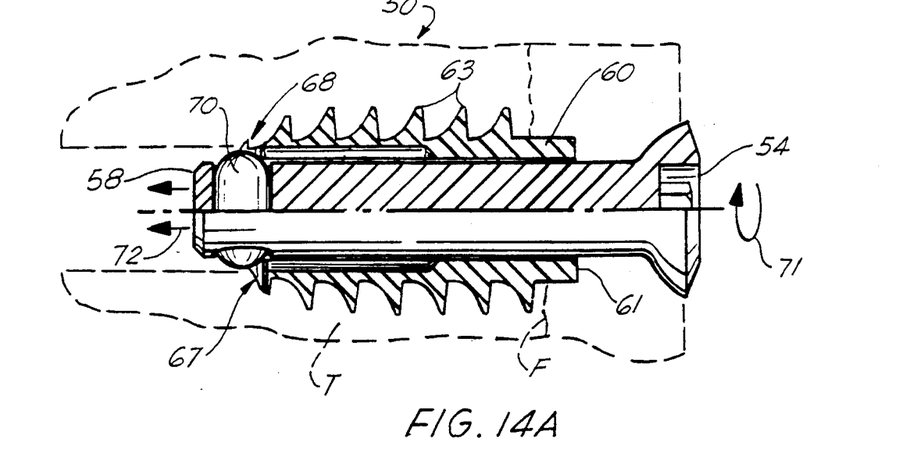
FIG. 14A-14C are sequential sectional side views illustrating installation of the second embodiment of the apparatus of the present invention.
Figure 14B:
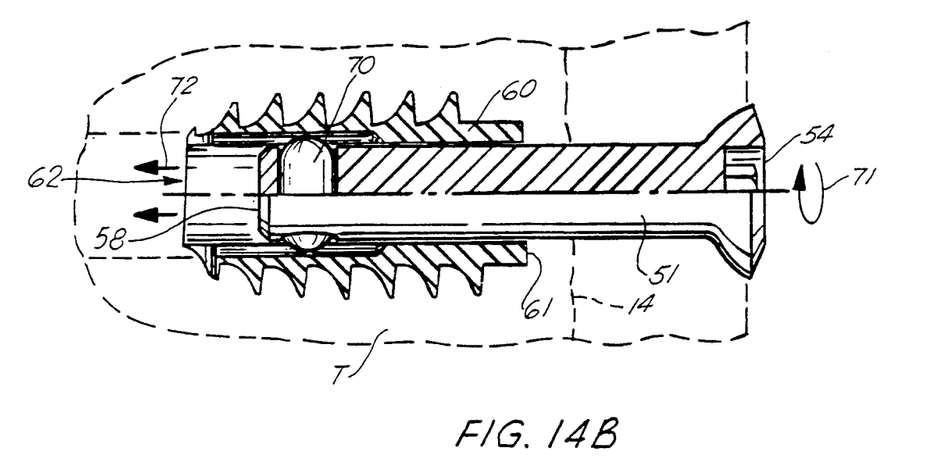
Figure 14C:
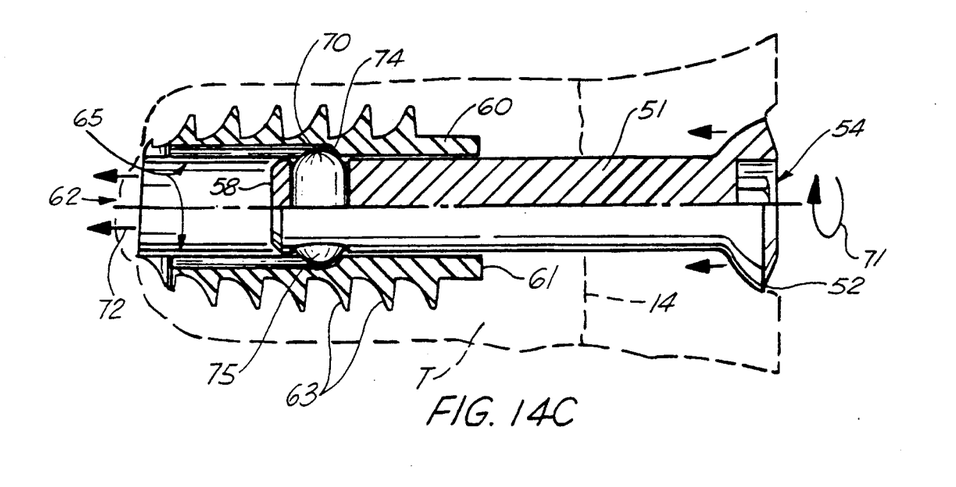

FIGS. 11-13 and 14A-14C illustrate an alternate embodiment of the apparatus of the present invention designated generally by the numeral 50. The compression screw apparatus 50 includes a shaft body 51 having an upper proximate enlarged end 52 that includes an upper dished or convex surface defined by annular inclined surface 53. The upper end 52 of the shaft body includes a tool socket 54 which can be, for example, a hexagonal socket receptive of a driver such as 19 shown in FIG. 6. In the embodiment of FIGS. 11-13, and 14A-14C, the driver registers with a closed socket that extends a short distance into the upper proximate end 52 of shaft body 51. The tool socket 54 would be symmetrically placed about the central longitudinal axis 55 of the shaft body so that torque can be imparted to the shaft body 51 using a driver 19, for example. Upper proximate enlarged end portion 52 includes a curved underside 56, and a curved transitional section 57 that meets with an enlongated generally cylindrical portion of the shaft body as shown in FIG. 11. The distal ends 58 of the shaft body is spaced a short distance from a transverse opening 59 which accommodates pin 70. Lag screw member 60 slidably mounts upon shaft body 51 as the internal bore 62 of lag screw member 60 as an internal diameter portion that registers upon and slides upon the outer surface of shaft body 51, as shown in FIGS. 11 12, and 14A-14C. The bore wall 54 is enlarged at longitudinal grooves 65 which are sized and shaped to accommodate the exposed portion 74, 75 of pin 70, as shown in FIGS. 14A-14C. The grooves 65 are open ended at the bottom 69 of lag screw member 60, but terminate at stop 66 which limit the extension of lag screw member 60 away from upper proximate enlarged end 52 of shaft body 51, the extended position being shown in FIG. 14C wherein the pin 70, and more particularly the ends 74 and 75 thereof register with the stops 66.

Arcuate recesses 67, 68 can be provided at the bottom of lag screw member 60 so that pin 70 can be moved transversely into and out of transverse opening 59 when sleeve 60 assumes a retracted fully withdrawn position upon shaft 51, the position shown in FIG. 14A.

FIGS. 14A-14C illustrate the installation of compression screw apparatus 50. In FIG. 14A, the lag screw 60 is in a fully retracted position, wherein arrow 71 indicates rotational torque that is imparted by the surgeon using a driver 19, for example, to rotate the entire assembly 50. As the assembly 50 is rotated, the threads 63 of lag screw member 60 bite into the surrounding bone tissue T and advance the lag screw member 60 in the direction of arrows 72. In FIG. 14B, a transitional position is shown wherein the lag screw member 60 has advanced about halfway between its fully retracted position of 14A and its fully extended position of 14C.

In FIG. 14C, the lag screw member 60 is fully extended and the transverse pin 70 registers against stops 66 of grooves 65 limiting further movement of the lag screw. At this point, the surgeon continues to impart torque to the at the socket 54 using a driver 19, for example. As the transverse pin 70 abuts the stops 66, resistance to continued rotation dramatically increases and a tension load is placed in the apparatus 50, along the length thereof.

PARTS LIST

-10-Compression screw apparatus
-11-Femur
-12-Neck
-13-Ball
-14-Fracture site
-15-Drill
-16-Drill bit
-17-Surgical opening
-18-Surgical opening
-19-Driver Tool
-20-Proximate end portion
-21-Angled head
-22-Annular inclined surface
-23-Shaft
-24-Transition
-25-Peripheral edge
-26-Annular shoulder
-27-Enlarged diameter annular end portion
-28-Bore
-29-Lower stop
-30-Lag sleeve
-31-Threads
-32-Upper end of lag
-33-Annular sleeve
-34-Internal cylindrical opening
-35-Annular shoulder
-36-Inner cylindrical wall
-37-Space
-38-Hexagonal socket
-39-Frustro-conical section of bore
-40-Bore
-41-Lower end of lag
-42-Hex drive
-50-Compression screw apparatus
-51-Shaft body
-52-Upper proximate enlarged end
-53-Annular inclined surface
-54-Tool socket
-55-Central longitudinal axis
-56-Curved underside
-57-Transition curved section
-58-Distal end of shaft body
-59-Transverse cylindrical opening
-60-Lag screw member
-61-Proximate end of lag screw
-62-Lag screw bore
-63-Lag screw threads
-64-Bore wall
-65-Longitudinal grooves
-66-Stop
-67-Arcuate recess
-68-Arcuate recess
-69-Distal end of lag screw
-70-Transverse pin
-71-Arrow, rotational movement
-72-Arrow, linear movement
-H-Handle
-X-Axis
-B-Angle
-A-Angle
-P-Plate
-T-Tissue Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as the invention is:

1. A compression bone screw apparatus comprising:
    a) an elongated cylindrical internal shaft member that includes a first smaller diameter portion and an enlarged diameter annular proximate end portion;
    b) the internal shaft member having a smooth internal bore extending longitudinally along the length of the internal shaft member;
    c) a generally cylindrical external lag screw member with an internal lag screw bore for receiving the internal shaft member, and that is slidably mounted in telescoping fashion upon the shaft member, and the lag screw member being extendable to a position spaced from the enlarged diameter annular proximate end portion thereof;
    d) external thread means on the lag screw member defining its maximum diameter for engaging a surgically formed opening in bone tissue;
    e) the lag screw bore being elongated so that the internal shaft member can extend into the lag screw bore along substantially the entire length of the lag screw member; and
    f) compression loading means for placing the assembly of the lag screw member and internal shaft member in compression when the lag screw member and internal shaft member are fully extended with respect to each other to a maximum overall length.

2. The apparatus of claim 1 wherein the elongated cylindrical shaft member includes a first smaller diameter portion of generally uniform diameter as defined by a cylindrical outer surface of the first smaller diameter portion.

3. The apparatus of claim 1 wherein the internal shaft bore is open ended, extending the full length of the shaft member.

4. The apparatus of claim 1 wherein the lag screw member provides an internal lag screw bore of variable diameter.

5. The apparatus of claim 1 wherein the lag screw is shorter in length than the shaft member.

6. The apparatus of claim 1 wherein the lag screw carries socket means at its distal end portion, and communicating with the internal bore of the lag screw.

7. The apparatus of claim 1 wherein the lag screw provides a socket at its lower, distal end portion, and the assembled compression bone screw has a common internal bore that allows access to the socket via the enlarged internal annular proximate end portion.

8. The apparatus of claim 1 wherein the compression loading means comprises in part cooperating shoulders of the shaft member and lag screw which abut when the lag screw and shaft member telescope with respect to each other to a fully extended, maximum length position.

* * * * *